United States Patent [19]

Mondello

[11] Patent Number: 5,629,170
[45] Date of Patent: May 13, 1997

[54] METHOD FOR DETECTING DEHALOGENATION OF HALOGENATED AROMATIC COMPOUNDS

[75] Inventor: Frank J. Mondello, Niskayuna, N.Y.

[73] Assignee: General Electric Company, Schenectady, N.Y.

[21] Appl. No.: 526,793

[22] Filed: Sep. 11, 1995

Related U.S. Application Data

[63] Continuation of Ser. No. 217,814, Mar. 25, 1994, abandoned.

[51] Int. Cl.$^6$ .................. C12Q 1/04; C12Q 1/02; C12Q 1/00; C12P 1/00
[52] U.S. Cl. .................. 435/34; 435/29; 435/4; 435/262; 435/170; 435/41
[58] Field of Search .................. 435/34, 29, 4, 435/262, 170, 41, 252.33, 252.34, 849, 848, 875, 876, 877

[56] References Cited

U.S. PATENT DOCUMENTS

| | | | |
|---|---|---|---|
| 3,779,866 | 12/1973 | Azarowicz | 435/262 |
| 4,477,570 | 10/1984 | Colaruotolo et al. | 435/262 |
| 4,654,303 | 3/1987 | Hagedorn | 435/68 |
| 4,761,376 | 8/1988 | Kula et al. | 435/262 |
| 4,843,009 | 6/1989 | Bopp | 435/262 |
| 4,876,201 | 10/1989 | Bedard et al. | 435/262 |
| 4,956,064 | 9/1990 | Evers et al. | 435/170 |
| 4,981,793 | 1/1991 | Johnson et al. | 435/170 |
| 4,999,300 | 3/1991 | Barton | 435/262 |
| 5,009,999 | 4/1991 | Bopp | 435/29 |
| 5,071,755 | 12/1991 | Nelson et al. | 435/262 |
| 5,227,069 | 7/1993 | Van Dort et al. | 435/262 |
| 5,232,596 | 8/1993 | Castaldi | 210/603 |

OTHER PUBLICATIONS

Havel et al, Appl Microbiol Biotech (1992) 38:pp. 129–134.
May et al, Appl and Environm Microbiol (Dec. 1992) vol. 58, No. 12, pp. 4051–4054.
Bedard et al., App. & Envir. Microbiol. 53, 1094–1102 (1987).
Van Dort et al., App. & Envir. Microbiol. 57, 1576–1578 (1991).

*Primary Examiner*—John Kight
*Assistant Examiner*—Louise Leary
*Attorney, Agent, or Firm*—William H. Pittman

[57] ABSTRACT

An assay method for screening microorganism-containing compositions for degradation capacity via the 2,3-dioxygenase pathway includes a first step of contacting the microorganism with a polychlorinated aromatic compound which is not susceptible to such degradation but which, when anaerobically dechlorinated, affords products which are susceptible to such degradation. The resulting product is contacted in a second step with an indicator microorganism encoding the first three steps but not the fourth step of the 2,3-dioxygenase route, and the presence of color in the resulting product is an indication that dechlorination took place in the first step. The presence in a test sample of halogenated aromatic compounds capable of degradation by the 2,3-dioxidase pathway can be determined by employing the second step alone.

6 Claims, No Drawings

METHOD FOR DETECTING DEHALOGENATION OF HALOGENATED AROMATIC COMPOUNDS

This application is a continuation of application Ser. No. 08/217,814 filed Mar. 25, 1994, now abandoned.

BACKGROUND OF THE INVENTION

This invention relates to the microbial degradation of halogenated aromatic compounds, and more particularly to a simple assay method for detecting such degradation.

Halogenated aromatic compounds are a genus of organic compounds including, for example, halogenated dioxins, halogenated dibenzofurans and halogenated biphenyls. Such compounds, or related molecular species containing such compounds as impurities, have been used in various ways in industry, but there are concerns about their possible biological effects on humans and other species.

A subgenus of such compounds is the mono- and polychlorinated biphenyls, sometimes generically designated "polychlorinated biphenyls" or "PCBs", which were in wide use as dielectric materials in capacitors and the like. After such use ceased, sizeable quantities of these compounds were discarded in landfills and waterways. Many of them are not rapidly biodegraded and further concern has been expressed about possible long-term effects of the discarded materials on the environment.

A common microbial degradation route for halogenated aromatic compounds, the 2,3-dioxygenase pathway, is effective with many mono-, di- and trihalogenated compounds. As applied to PCBs, it includes the following steps performed under aerobic conditions: (1) dioxygenase enzyme activity to insert two oxygen atoms at the 2- and 3-positions, forming a 2,3-dihydrodiol; (2) dihydrodiol dehydrogenase activity to re-aromatize the 2,3dihydrodiol to a 2,3-dihydroxybiphenyl; (3) meta-cleavage of said 2,3-dihydroxybiphenyl by 2,3-dihydroxybiphenyl dioxygenase to produce a substituted hexadienoic acid such as 2-hydroxy-6-oxo-6-phenylhexa-2,4-dienoic acid, such compounds being brightly yellow in color by reason of their high degree of conjugation. In a fourth step characteristic of many microorganisms, a hydrase enzyme cleaves said hexadienoic acid to produce colorless products including a benzoic acid.

While the 2,3-dioxygenase pathway is generally effective for degradation of compounds relatively low in halogen, it is not effective for some compounds, including 2,5,2',5'-tetrachlorobiphenyl and 4,4'-dichlorobiphenyl. Such compounds can, however, often be dehalogenated to products which are degraded by the 2,3-dioxygenase pathway. Dehalogenation is typically performed by anaerobic microbes, in river or lake sediment or the like where little or no oxygen is present. Other methods, including chemical methods, for the dehalogenation of such compounds are also available. It is then possible to expose the dehalogenation products to oxygen and to the action of 2,3-dioxygenase active microbes for further degradation. Hereinafter, the dehalogenation of highly halogenated species under anaerobic conditions is designated "anaerobic dehalogenation". Further degradation via the 2,3-dioxygenase pathway is designated "dioxygenase degradation" and molecular species capable of being so degraded are designated "dioxygenase-susceptible" species, while species incapable of such degradation are designated "non-dioxygenase-susceptible" species.

As examples of anaerobic dehalogenation mechanisms, various microorganisms in soils and waterway sediments are capable of dechlorinating 2,5,2',5'-tetrachlorobiphenyl to such compounds as 2,5,2'-trichlorobiphenyl, 2,2'-dichlorobiphenyl and 2-chlorobiphenyl, all of which are dioxygenase-susceptible. Similarly, anaerobic dechlorination of 4,4'-dichiorobiphenyl to the dioxygenase-susceptible 4-chlorobiphenyl is possible.

It has typically been very difficult to determine, at least for qualitative purposes, whether dehalogenation of PCBs has taken place and the extent thereof. Such operations as solvent extraction, centrifugation and gas chromatographic analysis of the products have been necessary. These procedures are time consuming and are poorly suited for screening large numbers of samples.

Thus, there is a need for a simple screening method to determine whether or not a given material contains microorganisms capable of anaerobically dechlorinating PCBs. There is also a need for screening soil samples and the like to determine whether dioxygenase-susceptible PCBs are present, whereupon it might be of value to subject the soils to aerobic microbial treatment to degrade such PCBs.

SUMMARY OF THE INVENTION

The present invention provides a simple method which may be used for these purposes. It is based on the fact that dehalogenation operations, both chemical and microbial, will convert non-dioxygenase-susceptible halogenated aromatic compounds to dioxygenase-susceptible congeners. The presence of the latter can then be detected upon aerobic incubation in the presence of bacteria capable of initiating the first three steps, but not the hydrase enzyme step, of the 2,3-dioxygenase pathway. Upon contact with such bacteria, the accumulation of yellow metabolites may be detected by simple visual or spectrophotometric means. The presence of yellow metabolites indicates that the 2,3-dioxygenase pathway has been initiated.

One aspect of the invention (hereinafter "microorganism embodiment") is a method for screening a test composition for the presence of microorganisms capable of anaerobically dechlorinating polychlorinated aromatic compounds, which comprises:

selecting, as a substrate, a polychlorinated aromatic compound which is not susceptible to degradation by the 2,3-dioxygenase pathway but which, when anaerobically dechlorinated, affords products which are susceptible to such degradation;

contacting said substrate with said test composition in a first contact step;

contacting the product of said first contact step with an indicator microorganism encoding the first three steps but not the hydrase enzyme step of the 2,3dioxygenase route, in a second contact step; and screening the product of said second contact step for the presence of colored species indicative of the presence in the product of said first contact step of molecular species susceptible to the 2,3-dioxygenase pathway.

Another aspect (hereinafter "PCB embodiment", although it may likewise be employed with non-PCB halogenated aromatic compounds) is a method for screening a test sample for the presence of halogenated aromatic molecular species capable of dehalogenation by the 2,3-dioxygenase pathway, which comprises:

contacting said test sample with an indicator microorganism encoding the first three steps but not the hydrase enzyme step of the 2,3-dioxygenase route; and screening the product of said contact for the presence of colored species indicative of the presence in said test sample of said molecular species.

DETAILED DESCRIPTION; PREFERRED EMBODIMENTS

A key feature of the microorganism embodiment of the method of this invention is the PCB employed as a substrate therein. It must be one which is not itself dioxygenase-susceptible but which, upon anaerobic dechlorination, affords dioxygenase-susceptible products. Among the known compounds having this property are the aforementioned 4,4'-dichlorobiphenyl and 2,5,2',5'-tetrachlorobiphenyl, which are often preferred.

In the first step of the microorganism embodiment, a sample of the substrate is placed in contact with the microorganism or material being tested for anaerobic dechlorination activity. The source of said microorganism or material is typically a sediment or soil harvested from a given geographical area, most often a waterway. Contact with the substrate, typically in a concentration of about 10–50 ppm., is under typical incubation conditions for the microorganism, said conditions being anaerobic and generally including ambient temperatures on the order of about 20°–35° C. If the test sample is effective for anaerobic dechlorination, the product of the first contact step will contain dioxygenase-susceptible compounds.

The conditions of the second contact step include exposure of said compounds to oxygen and an indicator microorganism capable of initiating the first three steps but not the hydrase enzyme step of the 2,3-dioxygenase pathway. Numerous suitable microorganisms are known; they include *Escherichia coil* strain FM4560 and Pseudomonas sp. strain FM206 deposits of which were made in the American Type Culture Collection on Aug. 31, 1995, under the ATCC designation (accession) numbers 69894 and 55704, respectively. In other respects, the second step conditions are similar to those employed in the first step.

Upon performance of the second contact step, the dioxygenase-susceptible compounds will be converted via the first three steps of the 2,3-dioxygenase pathway to highly colored, typical yellow products. The fourth or hydrase enzyme step of the 2,3-dioxygenase pathway will not occur to destroy said yellow products, since the indicator microorganism does not encode for that step. The presence of such products is, therefore, indicative of dechlorination activity in the first contact step, and therefore of the effectiveness of the test sample as an anaerobic dechlorinating agent.

The microorganism embodiment may also be employed to screen a microorganism for a specific type of dechlorinating activity; i.e., o-, m- or p-dechlorination. This may be effected by employing as a substrate a molecular species in which only a single type of activity will produce a dioxygenase-susceptible product.

The procedure for the PCB embodiment is similar to that for the microorganism embodiment, except that a material to be screened for the presence of dioxygenase-susceptible halogenated (preferably polyhalogenated and most preferably polychlorinated) aromatic compounds is the test sample. Thus, there is no benefit in performing an anaerobic dehalogenation step. The PCB embodiment is also effective to test for the presence of halogens other than chlorine, especially bromine and iodine.

The invention is illustrated by a series of examples in which 1-ml. cultures of *E. coil* strain FM4560, containing approximately $10^9$ cells, were added to a series of vials which were also charged with various PCB molecular species to a final concentration of 10 or 50 ppm. The vials were placed under aerobic conditions in a shaking incubator at 30° C. for up to 24 hours and were then examined for color formation. The results are given in the following table, with color formation being assigned a number from 0 to 4 according to intensity, with 0 being no color and 4 being high intensity color.

| Example | PCB species | 10 ppm. | 50 ppm. |
| --- | --- | --- | --- |
| 1 | 2,5,2',5'-Tetrachlorobiphenyl | 0 | 0 |
| 2 | 2,5,2'-Trichlorobiphenyl | 3 | 4* |
| 3 | 2,4'-Dichlorobiphenyl | 1 | 2 |
| 4 | 2,3-Dichlorobiphenyl | 1 | 2 |
| 5 | 2-Chlorobiphenyl | 1 | 2 |
| 6 | 4,4'-Dichlorobiphenyl | 0 | 0 |
| -7 | 4-Chlorobiphenyl | 2 | 3 |

*Color observed after 20 minutes.

It will be observed that no color was detected in Examples 1 and 6, in which the PCBs were 2,5,2',5'-tetrachlorobiphenyl and 4,4'-dichlorobiphenyl respectively. This is, of course, because they are non-dioxygenase-susceptible PCBs as previously noted. Many of the other PCBs examined are known to be dechlorination products of those two species. Thus, it is apparent that the method of this invention can be employed to determine whether the anaerobic dehalogenation step has taken place.

In another series of experiments, samples similar to those of Examples 1–7 were prepared and 100 mg. of soil was added to each sample. The soil obscured color formation, but such formation could be detected after settling of the soil or centrifugation of the sample. Thus, a soil separation step makes it possible to employ the method for the assay of microorganisms present in soil or other sediment.

What is claimed is:

1. A method for screening a test composition for the presence of microorganisms capable of anaerobically dechlorinating polychlorinated aromatic compounds, which comprises:

selecting, as a substrate, a polychlorinated aromatic compound which is not susceptible to degradation by the 2,3-dioxygenase pathway but which, when anaerobically dechlorinated, affords products which are susceptible to such dechlorination;

anaerobically contacting said substrate with said test composition in a first contact step;

aerobically contacting the product of said first contact step with an indicator microorganism selected from the group consisting of *E. coli* strain FM4560 and Pseudomonas sp. strain FM206 which encodes the first three steps but not the hydrase enzyme step of the 2,3-dioxygenase route, in a second contact step; and screening the product of said second step for the presence of colored metabolite compounds indicative of the presence in the product of said first contact step of polychlorinated aromatic compounds susceptible to the 2,3-dioxygenase pathway.

2. A method according to claim 1 wherein the substrate is 2,5,2',5'-tetrachlorobiphenyl or 4,4'-dichlorobiphenyl.

3. A method according to claim 2 wherein the substrate is 2,5,2',5'-tetrachlorobiphenyl.

4. A method for screening a test sample for the presence of halogenated aromatic compounds capable of dehalogenation by the 2,3-dioxygenase pathway, which comprises the steps of:

aerobically contacting said test sample with an indicator microorganism selected from the group consisting of *E. coli* strain FM4560 and Pseudomonas sp. strain FM206 which encodes the first three steps but not the hydrase enzyme step of the 2,3-dioxygenase route; and screening the product of said contacting step for the presence of colored metabolite compounds indicative of the presence in said test sample of said halogenated aromatic compounds.

5. A method according to claim 4 wherein the halogenated aromatic compounds are polyhalogenated.

6. A method according to claim 5 wherein the polyhalogenated aromatic compounds are polychlorinated.

* * * * *